United States Patent
Schindhelm et al.

(10) Patent No.: US 9,827,388 B2
(45) Date of Patent: Nov. 28, 2017

(54) METHODS AND APPARATUS FOR DETECTING AND TREATING RESPIRATORY INSUFFICIENCY

(75) Inventors: Klaus Henry Schindhelm, Glenhaven (AU); David John Bassin, Coogee (AU); Glenn Richards, Bella Vista (AU)

(73) Assignee: ResMed Limited (AU)

( * ) Notice: Subject to any disclaimer, the term of this patent is extended or adjusted under 35 U.S.C. 154(b) by 552 days.

(21) Appl. No.: 12/751,174

(22) Filed: Mar. 31, 2010

(65) Prior Publication Data

US 2010/0275921 A1 Nov. 4, 2010

Related U.S. Application Data

(60) Provisional application No. 61/214,843, filed on Apr. 29, 2009.

(51) Int. Cl.
*A61B 5/08* (2006.01)
*A61M 16/00* (2006.01)
*A61B 5/00* (2006.01)

(52) U.S. Cl.
CPC .......... *A61M 16/0051* (2013.01); *A61B 5/08* (2013.01); *A61B 5/7275* (2013.01);
(Continued)

(58) Field of Classification Search
CPC .......... A61M 16/00; A61M 2016/0021; A61M 2016/0039; A61M 2016/0036;
(Continued)

(56) References Cited

U.S. PATENT DOCUMENTS

| 5,704,345 A | 1/1998 | Berthon-Jones |
| 6,390,091 B1 | 5/2002 | Banner et al. |

(Continued)

FOREIGN PATENT DOCUMENTS

| DE | 102007039004 A1 | 3/2008 |
| JP | H09122084 A | 5/1997 |

(Continued)

OTHER PUBLICATIONS

European Search Report, EP 10 15 7989, dated Aug. 17, 2010.
(Continued)

*Primary Examiner* — Peter S Vasat
(74) *Attorney, Agent, or Firm* — Botos Churchill IP Law LLP

(57) ABSTRACT

Devices and systems provide methods of detecting a severity change in respiratory insufficiency (RI) or chronic obstructive pulmonary disease (COPD) condition of a patient. In an example embodiment, a detection monitoring device determines one or more severity change indicators based on a measure of supplied pressure or other representative measure determined by the device. The supplied pressure may optionally be determined during pressure treatment that satisfies a target ventilation. The supplied pressure or representative data may be compared to one or more thresholds that are selected to represent a change in the condition of the RI or COPD patient such as an exacerbation of a prior condition. Results of the comparisons may trigger one or more warnings or messages to notify a patient or physician of a pending change to the patient's RI or COPD condition so that the patient may more immediately seek medical attention to treat the condition.

32 Claims, 4 Drawing Sheets

(52) U.S. Cl.
CPC ....... *A61M 16/0069* (2014.02); *A61B 5/7264* (2013.01); *A61M 16/0006* (2014.02); *A61M 2016/0027* (2013.01); *A61M 2016/0036* (2013.01); *A61M 2205/3375* (2013.01); *A61M 2205/3569* (2013.01); *A61M 2205/3592* (2013.01); *A61M 2205/502* (2013.01); *A61M 2230/04* (2013.01); *A61M 2230/205* (2013.01); *A61M 2230/42* (2013.01); *A61M 2230/46* (2013.01)

(58) Field of Classification Search
CPC ...... A61M 2016/0069; A61M 16/0006; A61M 16/0051; A61M 16/0069; A61M 2016/0027; A61M 2205/3375; A61M 2205/3569; A61M 2205/3592; A61M 2205/502; A61M 2230/04; A61M 2230/205; A61M 2230/42; A61M 2230/46; A61B 5/085; A61B 5/08; A61B 5/7264; A61B 5/7275; A61B 5/087
USPC ............ 128/204.23, 204.21, 203.23, 203.24, 128/204.19, 204.18, 200.24; 340/539.12, 340/573.1; 600/533
See application file for complete search history.

(56) References Cited

U.S. PATENT DOCUMENTS

| | | | |
|---|---|---|---|
| 6,398,728 B1 | 6/2002 | Bardy | |
| 6,532,957 B2 | 3/2003 | Berthon-Jones | |
| 6,635,021 B1 | 10/2003 | Sullivan et al. | |
| 6,845,773 B2 | 1/2005 | Berthon-Jones et al. | |
| 6,951,217 B2 | 10/2005 | Berthon-Jones | |
| 7,225,809 B1* | 6/2007 | Bowen et al. | 128/204.21 |
| 7,551,078 B2* | 6/2009 | Carlson et al. | 340/539.12 |
| 7,810,497 B2* | 10/2010 | Pittman et al. | 128/204.23 |
| 8,297,281 B2* | 10/2012 | Farrugia | 128/204.23 |
| 2004/0210154 A1 | 10/2004 | Kline | |
| 2005/0061315 A1 | 3/2005 | Lee et al. | |
| 2005/0076615 A1* | 4/2005 | Wallis | 53/431 |
| 2007/0215146 A1* | 9/2007 | Douglas et al. | 128/200.24 |
| 2007/0293779 A1 | 12/2007 | Bardy | |
| 2008/0004906 A1* | 1/2008 | Klass et al. | 705/2 |
| 2009/0038616 A1* | 2/2009 | Mulcahy et al. | 128/204.23 |
| 2009/0050154 A1 | 2/2009 | Strothmann et al. | |
| 2010/0022911 A1* | 1/2010 | Wariar et al. | 600/561 |
| 2010/0258124 A1 | 10/2010 | Madaus et al. | |

FOREIGN PATENT DOCUMENTS

| | | |
|---|---|---|
| JP | 2006502774 A | 1/2006 |
| JP | 2007521889 A | 8/2007 |
| JP | 2008516702 A | 5/2008 |
| NZ | 552070 A | 11/2008 |
| WO | 96/32055 A1 | 10/1996 |
| WO | 98/52467 A1 | 11/1998 |
| WO | 2004034938 A1 | 4/2004 |
| WO | 2005077447 A1 | 8/2005 |
| WO | 2006-037184 A1 | 4/2006 |
| WO | 2006079152 A1 | 8/2006 |
| WO | 2007052108 A2 | 5/2007 |
| WO | 2008031822 A1 | 3/2008 |
| WO | 2008/138040 A1 | 11/2008 |
| WO | 2009026582 A1 | 2/2009 |

OTHER PUBLICATIONS

Vasilliou et al. in "Expiratory flow limitation during mechanical ventilation detected by the forced oscillation method", Eur Respir J, 1996, 9, 779-786.

Peslin et al. in "Respiratory mechanics studied by forced oscillations during artificial ventilation", Eur Respir J, 1993, 6, 772-784.

* cited by examiner

METHODS AND APPARATUS FOR DETECTING AND TREATING RESPIRATORY INSUFFICIENCY

CROSS REFERENCE TO RELATED APPLICATIONS

This application claims the benefit of the filing date of U.S. Provisional Patent Application No. 61/214,843 filed Apr. 29, 2009, the disclosure of which is hereby incorporated herein by reference.

FIELD OF THE TECHNOLOGY

The present technology relates to systems, methods and apparatus for detecting and/or treating conditions of respiratory insufficiency such as Chronic Obstructive Pulmonary Disease. More particularly, it relates to detecting changes in the severity of such conditions.

BACKGROUND OF THE TECHNOLOGY

Respiratory insufficiency affects millions of people. For patient's suffering from this condition, the lungs are unable to inspire sufficient oxygen or expel sufficient carbon dioxide to meet the needs of the cells of the patient's body. For example, Chronic Obstructive Pulmonary Disease ("COPD") affects approximately thirteen million Americans and ten million Europeans. COPD is a disease involving some damage to the lungs. The airways and the alveoli of the lungs can lose their elastic quality. Walls between alveoli can become destroyed or they can become inflamed. The airways of the lungs may also produce more mucus than usual, which can restrict airflow. This damage will typically manifest itself in some difficulty with breathing such as dyspnea. COPD patients typically experience coughing, with an expulsion of mucus, shortness of breath, wheezing and a feeling of tightness in the chest. Emphysema and chronic obstructive bronchitis may each be considered to be a form of COPD. Chronic obstructive bronchitis may be characterized by an inflammatory response in the larger airways of the lungs. Emphysema may be characterized by destruction of tissue of the lungs from an inflammatory response.

Cigarette smoking is considered a leading cause of COPD. Most people with COPD have some history of smoking. Extensive exposure to lung irritants, such as air pollution or chemical fumes, may also contribute to COPD.

COPD may develop slowly, with the symptoms worsening over time. COPD is a significant cause of disability. COPD can make it difficult to perform physical activities such as walking or exercise. Initially, the symptoms may be most evident during vigorous activities. However, as the disease progresses, symptoms may become more evident during milder activities and even while at rest. COPD may even lead to death. It is presently the fourth leading cause of death in the United States.

There is no presently known cure for COPD. There is no treatment for restoring the airways and alveoli of the lungs of a COPD patient to their pre-disease condition. However, treatments and lifestyle changes can help a COPD patient to feel more comfortable, continue to be active and impede the progression of the disease.

There are devices that may be useful in diagnosing a patient's COPD. For example, COPD may be diagnosed with spirometry. This typically involves measuring lung function by the measurement of the volume and/or speed (flow) of air that can be inhaled and exhaled. X-rays may show a hyperinflation of the lungs and can help to exclude other lung diseases. A pulmonary function test that includes lung volume and gas transfer can show hyperinflation. This can permit a differentiation between COPD with emphysema or COPD without emphysema. A computed tomography scan of the chest at a high resolution may show a distribution of emphysema in the lungs and can help to exclude other lung diseases.

Oximetery can also assist with the analysis by showing low oxygen levels or hypoxemia and/or high carbon dioxide levels or respiratory acidosis. A blood sample can also show a high blood count that may be a reaction to long-term hypoxemia (i.e., a reactive polythycaemia).

It will be appreciated that there is a need in the art for improved techniques and devices for addressing the conditions of patients suffering from respiratory insufficiency or COPD.

SUMMARY OF THE TECHNOLOGY

An aspect of certain example embodiments of the present technology relates to a system for detecting the presence of, or a change in condition (e.g., worsening or a change in severity) of respiratory insufficiency and/or Chronic Obstructive Pulmonary Disease. In one form this involves evaluating at least one severity change indicator. The indicator represents information about a respiratory insufficiency and/or chronic obstructive pulmonary disease condition of the patient.

In some embodiments of the technology, a method involves evaluating at least one respiratory insufficiency condition of a patient. In the method, at least one pressure characteristic of a patient's respiratory treatment during delivery of a pressure treatment therapy with a respiratory treatment apparatus or flow generator is measured. The method further includes evaluating at least one respiratory insufficiency condition change indicator or severity change indicator based on the at least one pressure measure. The indicator represents information about a severity change in the respiratory insufficiency condition of the patient. Automated means for the method may be implemented in an apparatus or system. In some embodiments, certain aspects of the method may be automated, semi-automated, manual or combinations thereof.

In some embodiments of the present technology, a device monitors a patient to evaluate the condition of a patient. The device typically includes at least one transducer or sensor to generate a signal representative of the pressure delivered by a flow generator. The device also includes a processor, coupled with the at least one sensor. The processor may be configured to control an evaluation of at least one change condition indicator based on a measure of pressure derived from the signal representative of pressure. The at least one indicator represents information about a severity change in a respiratory insufficiency condition of the patient. In some embodiments, the device may also optionally include a flow generator or positive airway pressure (PAP) device, controlled by the processor, configured to generate a flow of breathable gas at a pressure above atmospheric pressure to a patient interface.

In some embodiments of the system, device or method, the measure of pressure may be a measure of pressure generated by the respiratory treatment device in order to maintain, or substantially maintain, a target ventilation with the respiratory treatment apparatus. The target ventilation may be a minute ventilation, an estimate of gross alveolar ventilation, or an estimate of alveolar ventilation. Moreover, the evaluation of the severity change indicator may involve a threshold comparison of the measure of pressure. In some embodiments, the threshold comparison involves the measure of pressure and at least one prior measure of pressure used to maintain the target ventilation with the respiratory treatment apparatus. The threshold comparison may represent an indication of a repeated rise in the measure of pressure over a period of time, such as a period of hours, 1 day, 2 day, 3 day, 4 days, 5 days, or more.

In some embodiments of the device or method, the threshold comparison involves a difference between the measure of pressure and a prior measure of pressure used to maintain, or substantially maintain, the target ventilation with the respiratory treatment apparatus. The threshold comparison may also involve a ratio of the measure of pressure and a prior measure of pressure used to maintain the target ventilation with the respiratory treatment apparatus.

In still further embodiments of the device or method, the evaluation of the severity change indicator may also involve a further threshold comparison with a determined respiratory rate and a prior respiratory rate. This threshold comparison may represent an indication of a repeated rise in the determined respiratory rate over a period of time, for example over a period of hours, 1 day, 2 day, 3 day, 4 days, 5 days, or more.

In some embodiments of the method or device a warning may be generated based on the severity change indicator. The warning may be an activated light or a text or graphic or audible message or other means of communicating the information or combinations thereof. Optionally, an electronic message may be transmitted. The electronic message may include data representing a result of the evaluation of the severity change indicator.

In still further embodiments, a system monitors a patient to evaluate a respiratory insufficiency condition or chronic obstructive pulmonary disease condition of the patient. The system may include a flow generator configured to generate a flow of breathable gas at a pressure above atmospheric pressure to a patient interface. The system may also include a pressure means to generate a signal representative of the pressure delivered by a flow generator. Furthermore, a processing means is included for controlling an evaluation of a severity change indicator based on a measure of pressure derived from the signal representative of pressure. The indicator represents information about a severity change in the respiratory insufficiency condition or a chronic obstructive pulmonary disease condition of the patient.

Some embodiments of the present technology involve a system for monitoring a patient to evaluate a respiratory insufficiency condition of a patient. The system typically includes at least one sensor to generate a signal associated with a pressure therapy treatment of the respiratory system of patient. The system also may include a processor configured to control an evaluation of a severity change indicator based on a measure from the signal of the at least one sensor, such that the severity change indicator represents information about a change in severity of a respiratory insufficiency condition of the patient. The measure may represent the degree of respiratory assistance therapy determined from the signal of the at least one sensor. In some embodiments, the control of the evaluation of the severity change indicator may include assessing detected data associated with inspiratory flow limitation to rule out upper airway obstruction. Optionally, the control of the evaluation of the severity change indicator may include assessing a measure representing a respiratory rate. Still further, the control of the evaluation of the severity change indicator may include assessing a measure representing a respiratory duty cycle determined from the signal of the at least one sensor. Moreover, the control of the evaluation of the severity change indicator may optionally include assessing a measure representing an intrinsic positive end expiratory pressure. Similarly, the control of the evaluation of the severity change indicator may include assessing a measure representing an expiratory flow limitation. In some embodiments, the measure may represent a magnitude of a measured flow in a later portion of expiration that is determined from the signal of the at least one sensor and the control of the evaluation may further assess an absence of a change in respiratory rate or ventilation.

In some embodiments, a device for monitoring a patient to evaluate a respiratory insufficiency condition of a patient includes at least one sensor to generate a signal representative of one or more physiological characteristics of a patient and a processor, in communication with the at least one sensor. The processor is configured to control an evaluation of a severity change indicator based on one or more measures derived from the signal. The indicator represents information about a change in severity of a respiratory insufficiency condition of the patient.

Various aspects of the described example embodiments may be combined with aspects of certain other example embodiments to realize yet further embodiments.

Other features of the technology will be apparent from consideration of the information contained in the following detailed description, abstract and claims.

BRIEF DESCRIPTION OF TEE DRAWINGS

The present technology is illustrated by way of example, and not by way of limitation, in the figures of the accompanying drawings, in which like reference numerals refer to similar elements including:

DETAILED DESCRIPTION

The present technology involves methods and devices for the treatment of patients with respiratory insufficiency (RI) such as chronic obstructive pulmonary disease (COPD). The technology may be implemented to detect severity changes in the condition of the diseases. For example, some COPD patients suffer from exacerbation. Exacerbation may require modifications to medical treatment. Untreated exacerbation could lead to further exacerbation and potentially require hospitalization for the patient. However, if exacerbation is discovered early enough, such as at the earliest stages of its onset, it may be treated in a manner that may avoid hospitalization. The severity change indicator of the devices of the present technology provides a basis for detecting such changes in RI or COPD patients and for notifying the patient and/or medical providers of the potential need for medical intervention with respect to the respiratory insufficiency or chronic obstructive pulmonary disease condition of the patient.

Figure 1:
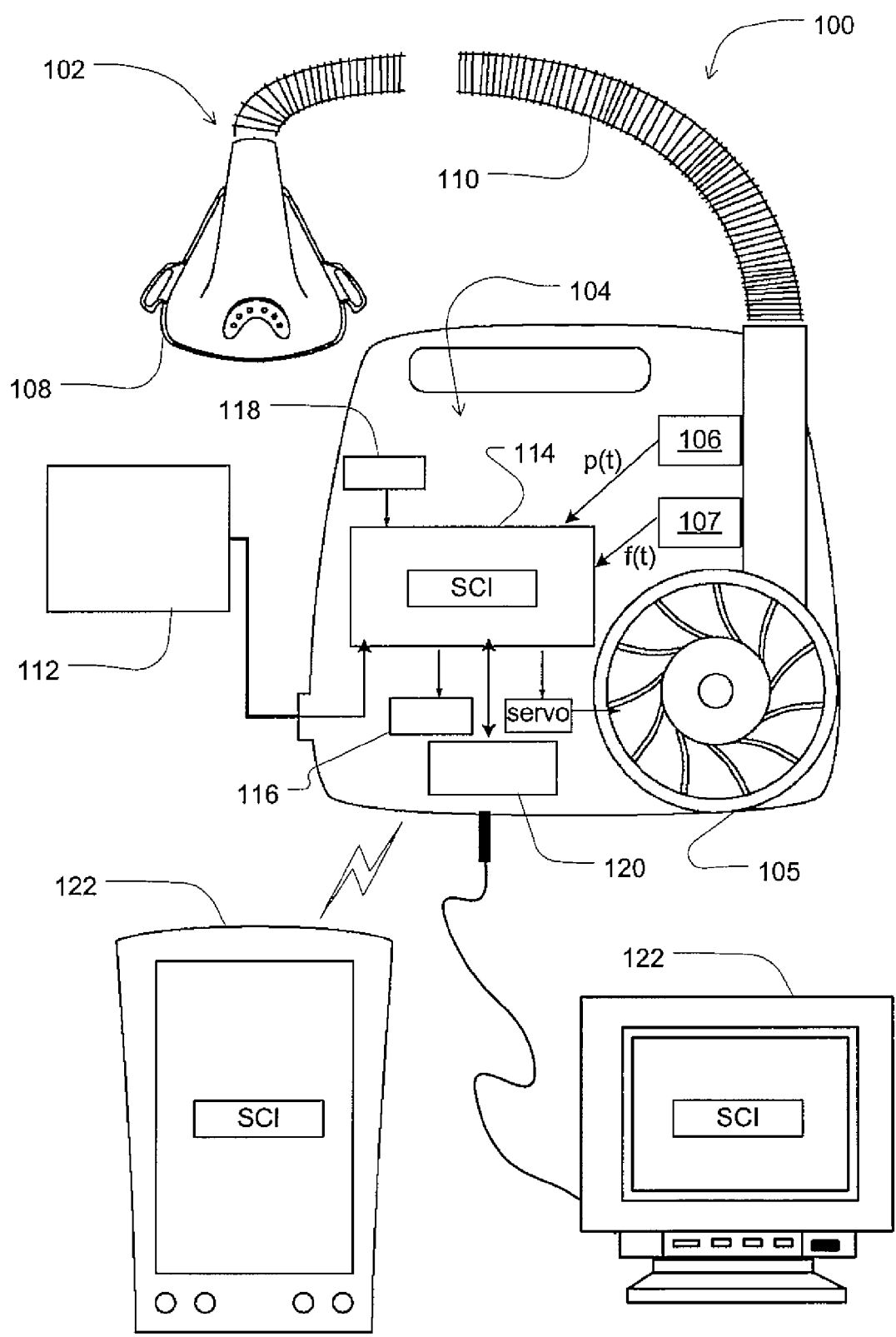
FIG. 1 illustrates example components of a monitoring device to implement a respiratory insufficiency or chronic obstructive pulmonary disease severity change indicator.

An example embodiment of a device for implementing one or more of the severity change indicators (SCI) of the present technology is illustrated in FIG. 1. In the embodiment, the detection device 100 implements a RI or COPD severity change indicator (referenced in FIG. 1 as "SCI"). The detection device 100 will typically include a patient respiratory interface 102, a delivery tube 110, a controller 104 and a flow generator such as a servo-controlled blower 105.

The patient respiratory interface such as a mask 108 as shown together with the delivery tube 110, provides a respiratory treatment to the patient's respiratory system via the patient's mouth and/or the patient's nares. Optionally, the patient respiratory interface may be implemented with a nasal mask, nose & mouth mask, full-face mask or nasal pillows or tracheostomy tube.

With the flow generator, the detection device 100 can be configured to generate a respiratory pressure treatment at the patient respiratory interface. To assist this end, the device may further include a pressure sensor 106, such as a pressure transducer to measure the pressure generated by the blower 105 and generate a pressure signal p(t) indicative of the measurements of pressure. In such a device, the delivery tube 110 may serve as the sense tube to permit detection of pressure levels supplied to the mask or patient respiratory interface.

The detection device 100 may also optionally be equipped with a flow sensor 107, which may be coupled with the patient respiratory interface. The flow sensor generates a signal representative of the patient's respiratory flow. The signals from the sensors may be used to detect obstructive or central apneas, hypopneas, cardiogenic airflow, respiratory rates and other respiratory related parameters from the signals measured by the sensors. In some embodiments, flow proximate to the mask 108 or delivery tube 110 may be measured using a pneumotachograph and differential pressure transducer or similar device such as one employing a bundle of tubes or ducts to derive a flow signal f(t). Alternatively, a pressure sensor may be implemented as a flow sensor and a flow signal may be generated based on the changes in pressure. Although the pressure or flow sensors are illustrated in a housing of the controller 104, they may optionally be located closer to the patient, such as in the mask 108 or delivery tube 110. Other devices for generating a respiratory flow signal or pressure signal may also be implemented. For example, a motor RPM sensor may be utilized to estimate pressure or flow information supplied by the flow generator device based upon the characteristics of the system.

Based on flow f(t) and/or pressure p(t) signals, the controller 104 with one or more processors 114 generates blower control signals. For example, the controller may generate a desired pressure set point and servo-control the blower to meet the set point by comparing the set point with the measured condition of the pressure sensor. Thus, the controller 104 may make controlled changes to the pressure delivered to the patient interface by the blower. Optionally, such changes to pressure may be implemented by controlling an exhaust with a mechanical release valve (not shown) to increase or decrease the exhaust while maintaining a relatively constant blower speed.

With such a controller or processor, the apparatus can be used for many different pressure treatment therapies, such as the pressure treatments for sleep disordered breathing, Cheyne-Stokes Respiration, obstructive sleep apnea (e.g., CPAP, APAP, Bi-Level CPAP, AutoVPAP), etc., or combinations thereof by adjusting a suitable pressure delivery equation. For example, the pressure treatment therapies of the devices described in U.S. Pat. Nos. 6,532,957, 6,845,773 and 6,951,217, which are incorporated herein by reference in their entireties, may be implemented with a COPD detection device 100 of the present technology. For example, as described in these patents, the controller and flow generator may be configured to ensure delivery of a specified or substantially specified target ventilation, for example, a minute ventilation, a gross alveolar ventilation or a alveolar ventilation, to the patient interface during the course of a treatment session by comparing an measure of ventilation with the target ventilation; or delivery of a tidal volume by comparing a measure of tidal volume with a target tidal volume. This may be accomplished with pressure variations that provide a bilevel form of therapy or some other form of therapy that may more smoothly replicate changes in a patient's respiration cycle.

Optionally, the detection device 100 may also include additional diagnosis sensors 112 that may assist in the evaluation of one or more severity change indicators of the present technology. For example, the device may include an oximeter. The oximeter may generate a signal representative of a blood oxygen level of a patient. A suitable example oximeter or monitor device may optionally be any of the devices disclosed in International Patent Application No. International Application No. PCT/AU2005/001543 (Pub. No. WO/2006/037184) or International Patent Application No. PCT/AU1996/000218 (Pub. No. WO/1996/032055), the disclosures of which are incorporated herein by cross-reference. As disclosed in these incorporated PCT applications, the monitor may serve as diagnosis sensors that can also optionally provide a blood pressure and/or heart or pulse rate monitor for measuring a heart rate and/or blood pressure of the patient.

In some embodiments, the diagnosis sensors may also include an ECG monitor. Such a device may be configured to detect cardiac-related characteristics such as a heart rate and may also determine respiratory parameters (such as central or obstructive apneas, hypopneas, etc.) Optionally, these parameters may be determined by the analysis algorithms of controller 104 based on transmission of the ECG data to the controller or they may be determined by the monitor and be transmitted to the controller 104.

In some embodiments, the diagnosis sensors may include a movement sensor. For example, a suprasternal notch sensor or chest band may be implemented to generate a movement signal that is indicative of patient effort during respiration. Other suitable sensors may include the movement sensing devices disclosed in International Patent Application No. PCT/AU1998/000358 (Pub. No. WO1998/052467), the disclosure of which is incorporated herein by cross-reference. The movement sensors thus may provide a measure of patient effort and/or respiration rate and may be used as an alternative to a flow sensor or in conjunction with other flow sensors in the determination of a severity change indicator as discussed in more detail herein.

In some embodiments, the diagnosis components may be equipped to determine measures of expiratory flow limitation by inducing oscillations in a patient's respiratory system. For example, the device may determine changes in real and imaginary impedance values between inspiration and expiration by analysis of pressure and/or flow measures during forced oscillations. For example, Fourier analysis maybe utilized. Other mathematical techniques for determining complex impedance based on such oscillations may also be implemented (e.g. suitably prefiltering then either windowing and calculating inner products with sine and cosine waves, or least-squares fitting of sine and cosine waves, etc.) Forced oscillations may be implemented by a controlled loudspeaker or amplifier as disclosed by Vasilliou et al. in "Expiratory flow limitation during mechanical ventilation detected by the forced oscillation method" (Eur Respir J, 1996, 9, 779-786) or Peslin et al. in "Respiratory mechanics studied by forced oscillations during artificial ventilation" (Eur Rospir J, 1993, 6, 772-784). Forced oscillations may be implemented in a flow generator such as is commonly used in CPAP or noninvasive pressure support ventilation, by suitably driving the fan motor. This technique is widely used in CPAP therapy as an element in the detection of upper airway obstruction, and specifically in the discrimination between closed (obstructed) and open (unobstructed) apnoeas (e.g. U.S. Pat. No. 5,704,345).

The signals from the sensors may be sent to the controller 104. Optional analog-to-digital (A/D) converters/samplers (not shown separately) may be utilized in the event that supplied signals from the sensors are not in digital form and the controller is a digital controller. Based on the signals from the sensor(s), the controller assesses the changing condition of the patient with one or more severity change indicators SCI.

The controller may optionally include a display device 116 such as one or more warning lights (e.g., one or more light emitting diodes). The display device may also be implemented as a display screen such as an LCD. Activation of the display device 116 will typically be set by the controller based on an assessment of the particular severity change indicators implemented by the detection device 100. The display device may be implemented to visually show information to a user of the detection device 100 or a clinician or physician. The display device 116 may also show a graphic user interface for operation of the detection device 100. User, clinician or physician control of the operation of the detection device 100 may be based on operation of input switches 118 that may be sensed by the controller or processor.

Optionally, the controller may also include a communications device 120 for receiving and/or transmitting data or messages by the detection device 100. For example, the communications device may be a wireless transceiver such as Bluetooth or WIFI transceiver. The communications device may also be a network communications device such as a phone modem and/or network card and may be implemented to send messages via the internet directly or through a computer to which the detection device may be docked. In general, the communications device 120 may be used to transmit warnings or messages to a clinician or physician assessable apparatus 122 such as a multi-patient monitoring system that allows a physician to review data from remote patient data recording devices such as the detection device 100. In these systems, a database may be provided to record patient monitoring data. Physicians or clinicians may receive a report, or warning that the patient may require closer observation, or should be brought to hospital.

The controller 104 or processor 114 will typically be configured to implement particular control methodology such as the algorithms described in more detail herein. Thus, the controller may include integrated chips, a memory and/or other control instruction, data or information storage medium. For example, programmed instructions encompassing such a control methodology may be coded on integrated chips in the memory of the device. Such instructions may also or alternatively be loaded as software or firmware using an appropriate data storage medium. With such a controller or processor, the device can be used for determining and analyzing many different parameters associated with the patient's condition based on data from the sensors. Thus, the processor may control the assessment of a severity change indicator as described in the embodiments discussed in more detail herein.

Figure 2:
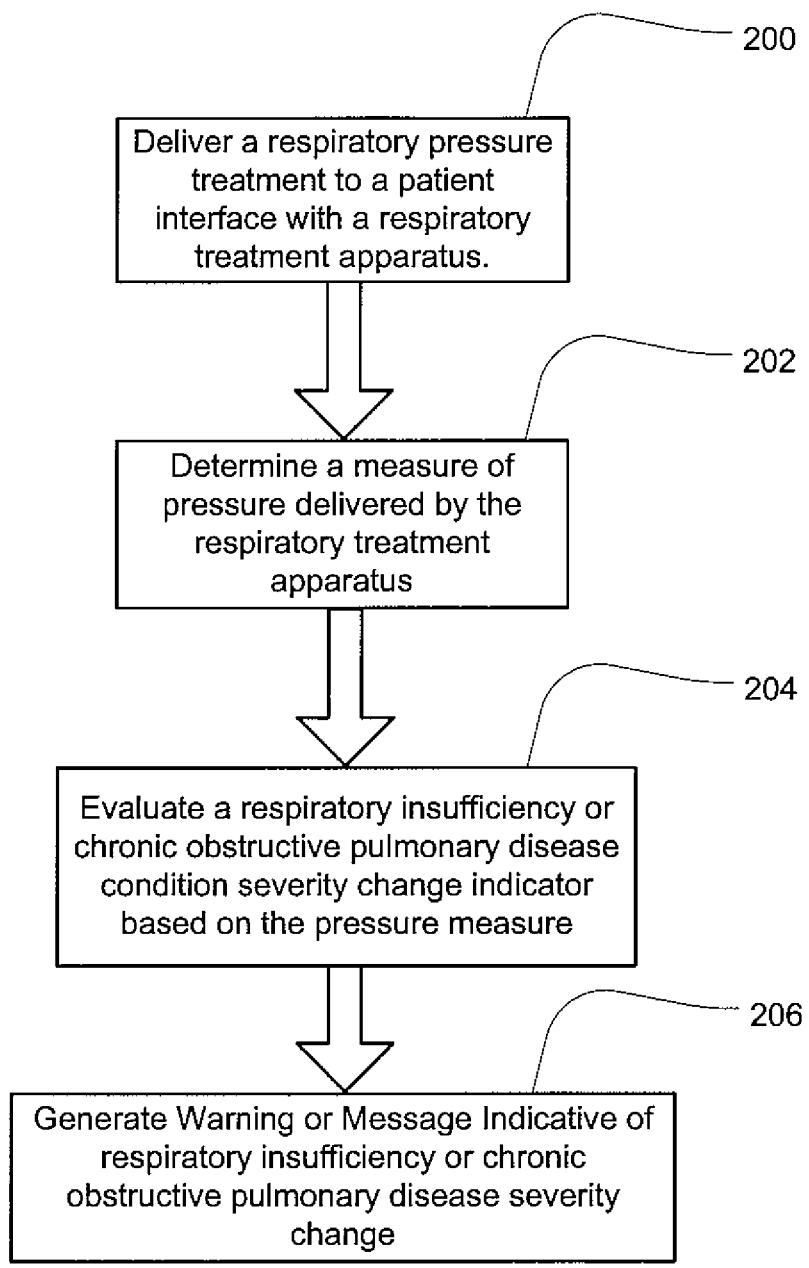
FIG. 2 is an example methodology for a device that implements a severity change indicator for detecting a condition of respiratory insufficiency patients.

One example methodology or algorithm of the controller 104 of the detection device 100 is illustrated in the flow chart of FIG. 2. In step 200 the detection device 100 may deliver a respiratory pressure treatment to a patient interface. For example, the processor may servo-control the flow generator to deliver a pressure treatment that satisfies a target ventilation. In such an embodiment, a target ventilation may be predetermined by a physician or automatically set with a learning mode of a respiratory treatment device. Thereafter, when a patient is being treated with the device, the device will measure delivered ventilation and adjust the pressure being supplied to the patient in a manner to ensure that the measured ventilation satisfies the target ventilation. Thus, if a patient's respiration causes the measured ventilation to begin to fall below or rise above the target ventilation over time, the flow generator will compensate with an increase or decrease respectively in the supplied pressure support.

During this treatment process, in step 202, the detection device 100 will monitor a measure of pressure delivered by the device. For example, based on a signal from a pressure transducer, the device may measure a supplied pressure or average pressure over a particular time period, such as the length of a treatment session (e.g., one day, one night, etc.) that was required to satisfy the target ventilation. This information may be recorded and associated with session identification information to identify the particular treatment session or date during which it was delivered, etc. The information may then be stored in the device for multiple sessions.

Based on the analysis algorithms implemented in the controller 104, the detection device will then evaluate a respiratory insufficiency or COPD severity change indicator based on the measured pressure in 204. For example, it may evaluate the one or more of the determined supplied pressure parameters with respect to one or more thresholds. Typically, each threshold is chosen so that the results of the comparison indicate a severity change in the RI or COPD condition of the patient such as the patient beginning to experience a level of RI or COPD exacerbation so that the patient can be considered for further RI or COPD treatment by a physician. For example, a determined pressure measure (e.g., an average supplied pressure in $cmH_2O$) from a current session with the device may be compared to one or more pressure measures of one or more prior sessions (e.g. an averaged pressure measure taken from one prior session or an averaged pressure measure taken from several prior treatment sessions.) A present change in the pressure measure (such as an increase or a certain amount of increase in the degree of respiratory assistance therapy) with respect to the previous determined pressure measure(s) may be taken as a severity change indicator.

By way of further example, inspecting for a continuous rise in the pressure support measure over a period of days, for example, by detecting continuous increases over several days of treatment by successively comparing a present measure with a prior measure through several treatment sessions (e.g., 3-7 treatment sessions), may be taken as a severity change indicator. Optionally, increases equal or greater to one or more predetermined threshold amounts may also be considered indicative of a change in the RI or COPD condition of the patient. These evaluations may indicate that the patient's RI or COPD condition should be considered by a physician for a change in RI or COPD treatment (e.g., a prescription medicine etc.).

These changes may be detected with comparison operations on historic pressure data. They may be detected by examining two or more such measures for equality. They may also be detected by determining differences between consecutive and/or successive sessions and comparing these to the predetermined thresholds. Similarly, comparisons may be implemented with ratios involving present pressure measures to one or more prior pressure measures and by assessing the result of the ratios against one or more thresholds such as a threshold that represents an amount of change. Thus, the thresholds may be selected to consider how significant the change or increases are such that small changes may be ignored. By way of further example, increases, or increases of a certain amount, in the supplied pressure for two or more consecutive days of monitoring sessions without a comparable decrease over the same consecutive day time frame in the following days may be taken as the COPD condition indicator.

Alternately, or in addition, a severity change indicator may be based on changes in other RI or COPD representative data or respiratory parameter(s) measured and tracked by the detection device 100 such as respiratory rate, respiration effort, blood gas levels, other measures, such as increased hours of use, or combinations thereof that may optionally be determined by the device. For example, an average respiration rate from a present session may be compared to prior sessions to determine change(s) or amount(s) of change in one or more comparisons like the comparisons of the pressure measure as previously described. For example, an increase in an average respiration rate in a current session may be determined from a comparison with a similarly determined respiration rate of a prior session, such as one or more prior monitoring sessions. Such changes may be taken as a RI or COPD severity change indicators of the present technology. By way of further example, increases, or increases of a certain amount, in the respiratory rate or other representative data for two or more consecutive days of monitoring sessions without a comparable decrease over the same consecutive day time frame in the following days may be taken as the severity change indicator.

In such cases, the degree of the change(s) and the length of time over which parameter change(s) have occurred may be assessed to determine the likelihood of acute exacerbation, which may be represented by, for example, a variable or index. For example, the index may represent or show a greater likelihood of acute exacerbation with larger degrees or amounts of change and/or longer periods or lengths of time over which the change(s) occur. Depending on parameters, larger increases and/or longer periods of time of change may represent a more likely acute exacerbation occurrence.

Optionally, a severity change indicator may be based on the results of the comparison of several thresholds and several different parameters. For example, an increase in the supplied pressure over several sessions coupled with an increase in the respiration rates or some other change in other representative measures determined over several sessions may collectively be taken as a RI or COPD severity change indicator. Thus, any combination of the conditions of the indicators discussed herein may be implemented as a severity change indicator of the present technology.

Thresholds associated with these supplied pressure, respiratory rate or other representative data measures may be determined through empirical analysis of the conditions and changes experienced by RI or COPD patients. For example, they may be determined through an analysis of RI or COPD patients who are being treated by a respiratory treatment apparatus that supplies a target ventilation and by associating data from these measures with a change or exacerbation in the RI or COPD condition of the patient.

By way of further example, a severity change indicator based on other representative data may involve the monitoring of the patient's respiratory duty cycle (e.g., a ratio of the time of inspiration to the total time of a respiratory cycle (inspiration and expiration)) Such a measure may be denoted as Ti/Ttot. For example, a decrease in Ti/Tot may be considered as being related to a change in severity of RI or COPD.

Similarly, detected or monitored changes in intrinsic positive end expiratory pressure ("Intrinsic PEEP" or "PEEPi") may be evaluated for a severity change indicator. The intrinsic positive end expiratory pressure is a pressure needed to overcome expiratory flow limitation. In an example embodiment, the detection device may calculate one or more measures indicative of intrinsic PEEP, such as a measure of expiratory flow limitation (e.g., changes in real and/or imaginary impedance values between inspiration and expiration determined with a forced oscillation technique that may be periodically performed during treatment). Such a device may not attempt to treat the intrinsic PEEP but may use these measures, and/or changes thereto, directly as an indication of worsening COPD or RI. If the device does attempt to treat the PEEPi by adjusting an end expiratory pressure (EEP), an increase in EEP generated by a treatment control algorithm that seeks to reduce one or more measures of intrinsic PEEP may also be analyzed for an indication of a severity change in RI or COPD. In some embodiments, the residual untreated intrinsic PEEP in such a therapeutic device, which may optionally be combined with the increase in EEP provided by the treatment control algorithm, may also be evaluated for change as a COPD or RI severity change indicator. In such embodiments, the periodic determinations of PEEPi may be made within a monitoring or treatment session or between monitoring or treatment sessions so that the changes may be evaluated from several sessions and/or within a session.

In still another embodiment, an increase in the magnitude of a measured flow taken in the later parts (e.g., data samples) of expiration may be evaluated as severity change indicator of the present technology. In such a case, such an increase may indicate a severity change if the detected increase is not explained satisfactorily by other changes such as a change in respiratory rate or ventilation. Thus, such an increase in measured flow without a change or significant change in respiratory rate and/or ventilation may be deemed to indicate a severity change in RI or COPD.

In some embodiments, evaluation of one or more severity change indicators of the present technology may involve an algorithm that examines the rate of change of the recorded measures such as by implementing a Gaussian or other smoothed derivative calculation (e.g. a convolution with derivative of a Gaussian). Such evaluations of change may be more tolerant of occasional deviations with respect to a threshold so as to avoid false detections or indications of a severity change. Other means of detecting a significant increase in a quantity include regression analysis, where a statistically significant gradient (at some nominated significance level) of at least a certain value may be regarded as indicating a significant change of severity. Similarly, the algorithm may apply pattern classification techniques (e.g., fuzzy logic, categories with boundaries in feature space not parallel to axes, measures of distance from boundaries, etc. (e.g., any technique described in "Pattern Classification" (2nd ed.), by Duda, Hart and Stork) to provide a higher sensitivity and specificity, reduce sensitivity to noise and to outliers, and give a more progressive response in the detection of the severity change in the respiratory insufficiency or COPD. For example, Fuzzy classifier functions may be implemented to detect both a small change in a respiratory rate (RR) with a moderately large change in pressure support (PS) as a severity change indicator that may trigger a warning.

By way of further example, an increase in pressure support or the degree of respiratory assistance therapy may be due to an increase in upper airway resistance, especially that related to decrease in upper airway tone leading to partial or total upper airway obstruction. To avoid an undesirable level of false positive diagnoses of worsening of respiratory insufficiency of the patient, the severity change indicator evaluation may further involve data analysis that rules out severity change for RI or COPD by considering other data. For example, the analysis may consider the possibility of upper airway obstruction that may be the cause of the increase in respiratory treatment assistance rather than respiratory insufficiency. For example, the detection device may analyze a respiratory flow shape to detect inspiratory flow limitation that can be indicative of upper airway obstruction. If a significant increase in upper airways resistance is detected, an increase in respiratory assistance therapy would then not be taken to indicate a worsening in the respiratory insufficiency condition. In such a case, the severity change indictor might not indicate a change in severity of the patient's RI or COPD condition. If upper airway obstruction is not so detected in the presence of a certain increase in a degree of respiratory assistance therapy, then the severity change indicator may be taken to indicate a change in RI or COPD severity.

An apparatus or monitoring device 100 in accordance with the invention provides a convenient way to monitor patients and may be utilized while they sleep. Thus, in optional step 206 of FIG. 2, when the device determines that a change in the patient's condition is a worsening state of the patients RI or COPD based on the severity change indicators SCI, the indicators may be used to trigger the device to provide a warning or message in a form suitable for the patient and/or clinicians to be aware of the status of the patient's situation so that the patient may more efficiently receive the care that is necessary.

The warning or messaging of the system may take a number of forms. For example, the controller, in response to an affirmative severity change indicator, may activate a status light (e.g., an LED or an icon on a display screen or LCD) of the monitoring device. A more detailed message concerning the assessment of the indicator may also be displayed on the display screen. Optionally, the controller may also, or alternatively, send a message to a clinician or physician. Such a message may take the form of a wired or wireless communication. For example, the controller may generate a message via a paging system such as by automatically dialing a paging system. The controller may also be configured to generate an automated voice phone call message. The controller may also send the message by a fax transmission. In some embodiments, the controller may also send a message via any internet messaging protocol, such as an email message, or by any other internet data file transport protocol. The messages may even be encrypted to keep patient information confidential. A typical message may identify the patient. Such a message may also include the data of the changes recorded by the system of any other recorded patient information. The message may even express that the patient should be considered for additional RI or COPD treatment or an evaluation due to the detection of a potential exacerbation of RI or COPD.

Figure 3:
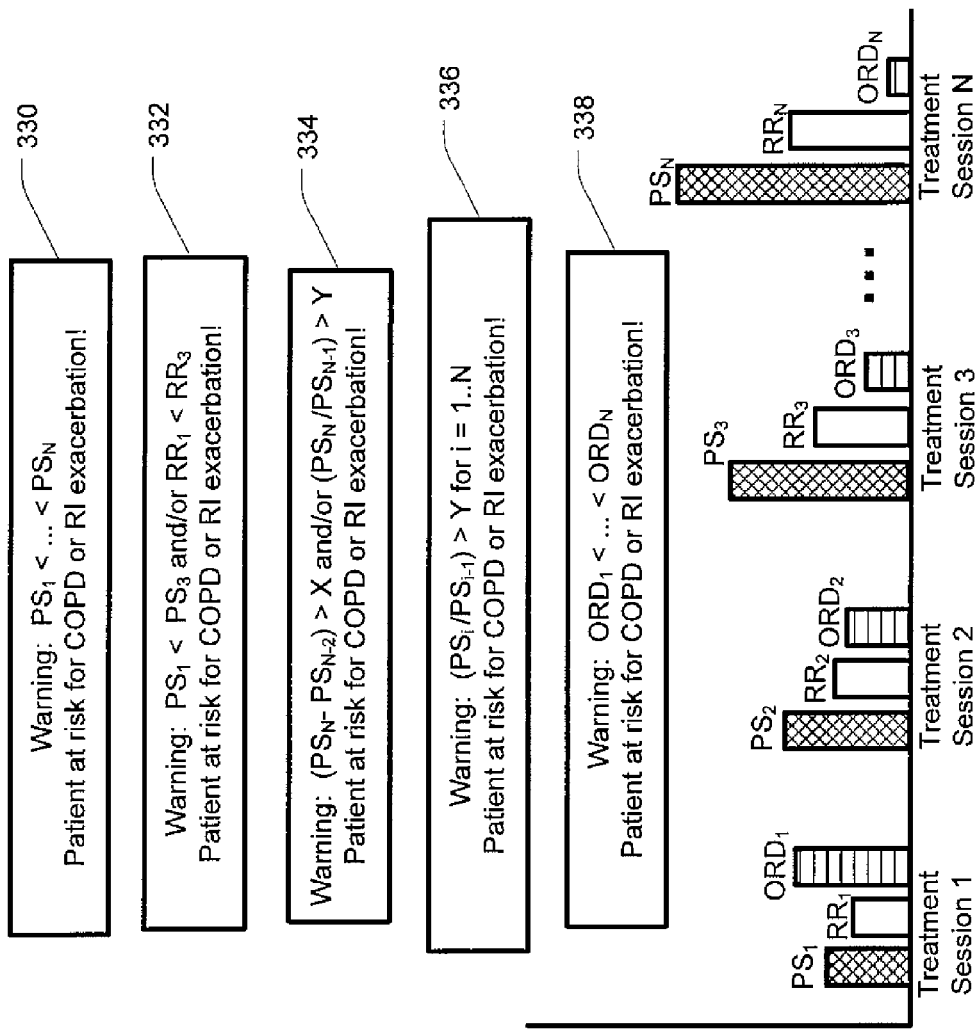
FIG. 3 illustrates several example severity change indicators and warnings suitable for use in embodiments of the present technology.

Thus, an example embodiment of a display or warning that may be presented to a patient or physician by the device may be a warning message such as a graphic or textual message. The message may be displayed on the device or a remote device based on the evaluation of one or more of the programmed severity change indicators SCI. Several example messages 330, 332, 334, 336, 338 are illustrated in FIG. 3. The message 330 is based on changes in the measured pressure supply (shown in FIG. 3 as "PS") over several days, such as consecutive or subsequent periods of use. The message 332 is based on a comparison between supplied pressure measures and respiratory rate (RR) measures for subsequent treatment periods. The message 334 is based on comparisons between differences or ratios of supplied pressure measures and additional thresholds (shown in FIG. 3 as Y and X) subsequent treatment periods. The message 336 is based on continuous consecutive increases in the supplied pressure by a factor Y for multiple treatment sessions. The message 338 is based on a continuous decrease in other representative data measures over several treatment sessions. Such other representative data measures are shown are shown in FIG. 3 as "ORD". Still optionally, a single message may also be based on a collective combination of two or more of the example changes illustrated in these messages such that the warning message is triggered only when the combination of conditions are met.

While a simple warning message may be utilized, graded levels of warning messages may also be generated to describe the patient's condition as multiple different severity change indicators or a repeated severity change indicators collectively triggers the different messages based on the severity of the detected conditions. For example, one severity change indicator may trigger an initial warning message on a certain day. However, a different message, such as one with a higher level of urgency, may be generated by a second and different severity change indicator on a subsequent day. For example, a different message may be generated as the number of days of increases in a supplied pressure also increases. In such an embodiment, after the first message, the second message may more urgently warn that the patient should immediately contact a physician for a medical examination. In this manner, the device may monitor or store data concerning each warning so that the warnings may be progressively altered or generated based on prior warnings and/or historic severity change indicators.

Furthermore, while all of these messages could be directed by the controller 104 to the patient via the display device 116 of the detection device 100 and the physician via the communications device 120, in some embodiments, the messages could be directed more selectively. For example, the first message may be only transmitted to a physician or clinician by only transmitting the message to a physician system 122 through the communications device 120 without showing it on the display device 116. However, the second message, which may be a more urgent message, could then be actively displayed on the display device 116 in addition to transmitting it to the physician system 122. An audible alarm from an optional speaker controlled by the controller of the device may also be implemented. Use of an audible alarm may depend on the urgency of the message.

Figure 4:
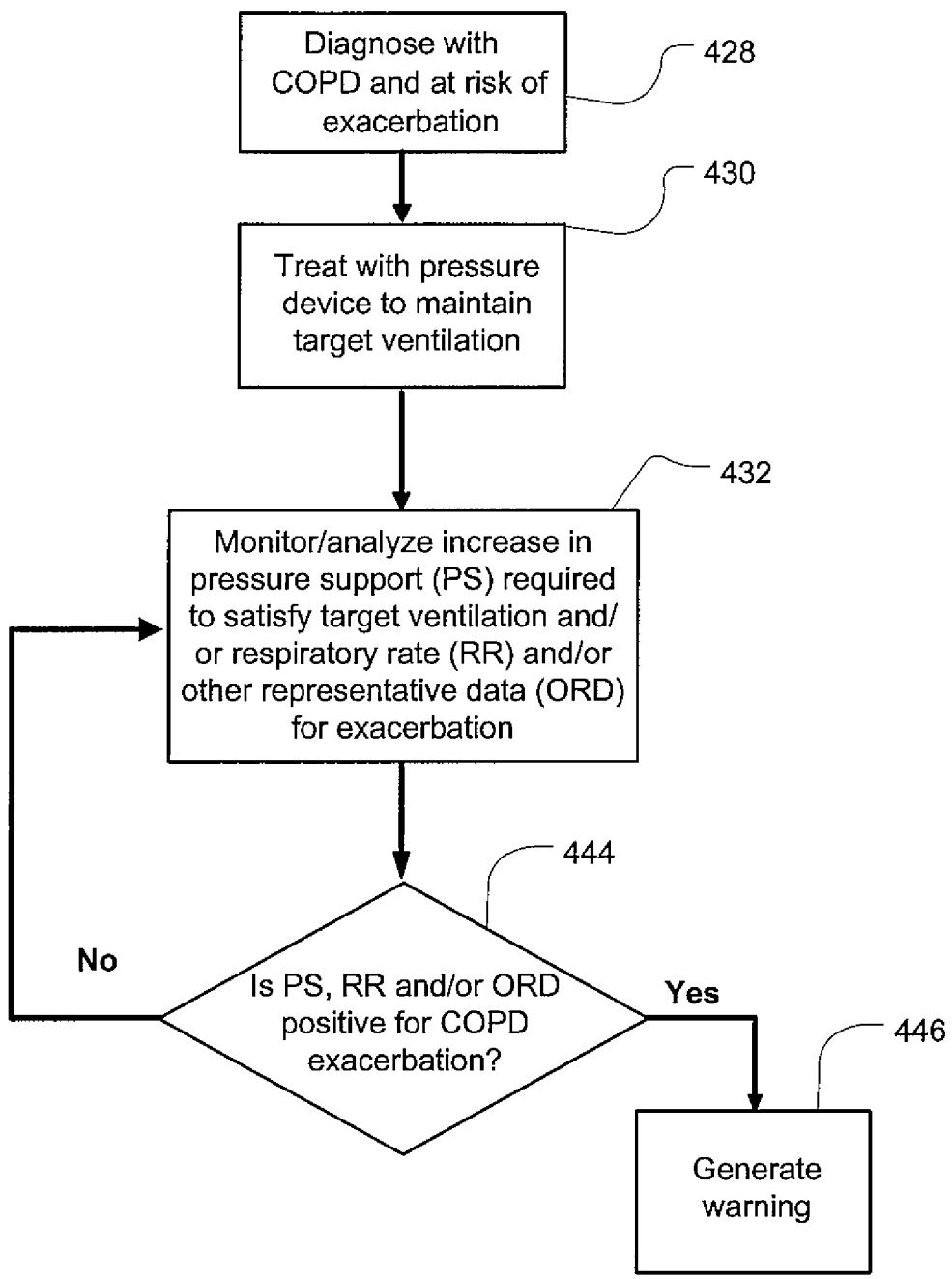
FIG. 4 is an example diagnosis flowchart for implementing treatment with devices that incorporate one or more the COPD severity change indicators of the present technology.

An example clinical methodology for prescribing and using some embodiments of the present technology is illustrated in FIG. 4. In step 428, a patient is diagnosed with an RI such as COPD and may be at a risk of experiencing exacerbation. In step 430, the patient is treated with a pressure therapy treatment to maintain a target ventilation such as a minute ventilation. In step 432, a device would monitor and analyze information based on the pressure treatment to determine the measures for the COPD condition indicators as previously discussed. In step 444, the thresholds of one or more severity change indicators would be evaluated. If a severity change indicator suggests that the patient is experiencing a worsening or change of the condition such as an exacerbation event, a warning would be triggered in step 446. However, if the severity change indicators do not suggest the presence of such a change in condition, no warning would be generated and the device would continue to monitor and analyze by returning to step 432. In this way, the present technology may be realized in different devices depending on the needs of the patient while taking advantage of the existing components of other devices that the patient may need.

In some embodiments of the present technology, one or more indicators may be generated based on data determined from a patient with or without the use of a pressure treatment therapy device. For example, a processing device may monitor increased exacerbations for respiratory insufficiency or COPD with the determination of a RI or COPD severity change indicator discussed herein. Such a monitor device may include at least one sensor to detect changes in movement, pressure, respiratory rate, heart rate etc. For example, a non-contact biomotion sensor may be used, such as BiancaMed's Doppler device which uses low power pulses of radio frequency energy transmitted and reflected back to a sensor to detect respiration rate, heart rate and movement. Alternatively, or in addition thereto, other respiratory monitoring devices such as a respiratory band may be used to detect increased effort and/or increased exertions. The measured data may then serve as a basis for the RI or COPD severity change indicators as previously discussed. This detected data may optionally be combined with other data determined by other sensors in the determination of the severity change indicators. The monitor device may optionally be utilized to determine the indicator without a respiratory treatment apparatus. Alternatively, such a monitor or non-contact sensor may be configured as part of a respiratory treatment apparatus or an external component that may transmit data (e.g., via wireless or wired communications link) to a respiratory treatment apparatus (e.g., ventilator) here the treatment apparatus and/or monitor determines an indicator of the present technology. Still optionally, the monitor device may be configured to transmit the data and/or indicators to a physician system, such as via an internet interface or other communications interface (e.g., via a wired and/or wireless link).

By way of further example, embodiments of the aforementioned technology may be implemented as an apparatus adapted to determine the likelihood of an acute exacerbation occurring in a patient with respiratory insufficiency. Such an apparatus may include at least one sensor adapted to measure at least one respiratory parameter of the patient. A controller of the apparatus, which may be coupled to the at least one sensor, may be configured to evaluate the respiratory parameter measured at an at least one earlier first time with the respiratory parameter measured at a second time to determine when changes in the respiratory parameter are occurring. When a change in the respiratory parameter is determined, the level or degree of change and the length of time between the at least one first time and second time are evaluated by the controller to determine the likelihood of an acute exacerbation occurring. In some such embodiments, the larger the level or degree of change in the respiratory parameter and the longer the length of time, the more likely an acute exacerbation is said to occur. In this regard, the change in the respiratory parameter may be an increase over time. Moreover, in some such embodiments, the respiratory parameter measured at a second time is evaluated with the respiratory parameter measured at multiple earlier first times to determine a change trend in the respiratory parameter over time. Further, the controller may be configured to provide a warning signal based on the determined likelihood of an acute exacerbation occurring. In addition, the apparatus may optionally include a flow generator that is adapted to provide positive pressure support to the patient.

While the RI or COPD severity change indicator technology has been described in several embodiments, it is to be understood that these embodiments are merely illustrative of the technology. Further modifications may be devised within the spirit and scope of this description. For example, while an integrated device is contemplated by the present technology, the methodology of the components of the devices may be shared across multiple components of a system. For example, a monitoring device, that may or may not be separate from a pressure treatment delivery device, may simply measure the physiological data from the patient and transfer the data to another processing system. The second processing system may in turn analyze the data to assess the indicators of the present technology. The second processing system may also evaluate the indicators and generate warning messages as described herein, such as by sending one or more of the described messages, in electronic form for example, back to the patient monitoring device for display on the device to warn the patient. Other variations can be made without departing with the spirit and scope of the technology.

Additional example embodiments may also be understood upon consideration of the following descriptive paragraphs. To this end, the technology may also involve:

A method for evaluating a respiratory insufficiency condition of a patient comprising: delivering a respiratory pressure treatment to a patient with a respiratory treatment apparatus; determining a measure of pressure delivered by the respiratory treatment apparatus; and evaluating a severity change indicator based on the pressure measure, the indicator representing information about a severity change in a respiratory insufficiency condition of the patient.

The method of any of the preceding paragraphs wherein the measure of pressure comprises a measure of pressure generated by the respiratory treatment device in order to maintain a target ventilation with the respiratory treatment apparatus.

The method of any of the preceding paragraphs wherein the target ventilation is a minute ventilation.

The method of any of the preceding paragraphs wherein the target ventilation is an estimate of alveolar ventilation.

The method of any of the preceding paragraphs wherein the target ventilation is an estimate of gross alveolar ventilation.

The method of any of the preceding paragraphs wherein the evaluating of the severity change indicator comprises a threshold comparison of the measure of pressure.

The method any of the preceding paragraphs claim 2 wherein the threshold comparison involves the measure of pressure and a prior measure of pressure used to maintain the target ventilation with the respiratory treatment apparatus.

The method of any of the preceding paragraphs wherein the threshold comparison represents an indication of a repeated rise in the measure of pressure over a period of days.

The method of any of the preceding paragraphs wherein the threshold comparison involves a difference between the measure of pressure and a prior measure of pressure used to maintain the target ventilation with the respiratory treatment apparatus.

The method of any of the preceding paragraphs wherein the threshold comparison involves a ratio of the measure of pressure and a prior measure of pressure used to maintain the target ventilation with the respiratory treatment apparatus.

The method of any of the preceding paragraphs wherein the evaluating of the severity change indicator further comprises a further threshold comparison involving a determined respiratory rate and a prior respiratory rate.

The method of any of the preceding paragraphs wherein the further threshold comparison represents an indication of a repeated rise in the determined respiratory rate over a period of days.

The method of any of the preceding paragraphs further comprising generating a warning based on the severity change indicator.

The method of any of the preceding paragraphs wherein the warning comprises an activated light.

The method of any of the preceding paragraphs wherein the warning comprises a message.

The method of any of the preceding paragraphs further comprising transmitting an electronic message including data representing a result of the determining of the severity change indicator.

A device for monitoring a patient to evaluate a respiratory insufficiency condition of the patient comprising: a transducer to generate a signal representative of the pressure delivered by a flow generator; and a processor, coupled with the sensor, the processor configured to control an evaluation of a severity change indicator based on a measure of pressure derived from the signal representative of pressure, the indicator representing information about a change in severity of a respiratory insufficiency condition of the patient.

The device of any of the preceding paragraphs further comprising a flow generator configured to generate a flow of breathable gas at a pressure above atmospheric pressure to a patient interface, wherein the processor is configured to control the flow generator.

The device of any of the preceding paragraphs wherein the flow generator is configured to generate the flow of breathable gas at a pressure above atmospheric pressure to maintain a target measure of ventilation, and wherein measure of pressure comprises a measure of pressure generated by the flow generator in order to maintain the target ventilation.

The device of any of the preceding paragraphs wherein the target ventilation is a minute ventilation and the measure of pressure is an average pressure.

The device of any of the preceding paragraphs wherein the target ventilation is an estimate of alveolar ventilation.

The device of any of the preceding paragraphs wherein the evaluation of the severity change indicator comprises a threshold comparison of the measure of pressure.

The device of any of the preceding paragraphs wherein the threshold comparison involves the measure of pressure and a prior measure of pressure used to maintain a target ventilation during a prior treatment session with the device.

The device of any of the preceding paragraphs wherein the threshold comparison represents an indication of a repeated rise in the measure of pressure over a period of days.

The device of any of the preceding paragraphs wherein the threshold comparison involves a difference between the measure of pressure and a prior measure of pressure used to maintain the target ventilation during a prior treatment session with the device.

The device of any of the preceding paragraphs wherein the threshold comparison involves a ratio of the measure of pressure and a prior measure of pressure used to maintain a target ventilation during a prior treatment session with the device.

The device of any of the preceding paragraphs wherein the evaluation of the severity change indicator further comprises a further threshold comparison involving a determined respiratory rate and a prior respiratory rate.

The device of any of the preceding paragraphs wherein the further threshold comparison represents an indication of a repeated rise in the determined respiratory rate over a period of days.

The device of any of the preceding paragraphs wherein the processor is configured to activate a warning based on the severity change indicator.

The device of any of the preceding paragraphs wherein the warning comprises an activated light.

The device of any of the preceding paragraphs wherein the warning comprises a message.

The device of any of the preceding paragraphs wherein the processor is configured to control transmitting of an electronic message including data representing a result of the evaluation of the severity change indicator.

The device of any of the preceding paragraphs further comprising a transmitter coupled with the processor, wherein the processor is further configured to control transmitting of a message including data representing the severity change indicator.

A system for monitoring a patient to evaluate a respiratory insufficiency condition of the patient comprising: a pressure means to generate a signal representative of the pressure delivered by a flow generator; and processing means for controlling an evaluation of a severity change indicator based on a measure of pressure derived from the signal representative of pressure, the indicator representing information about a change in severity of a respiratory insufficiency condition of the patient.

The system of any of the preceding paragraphs further comprising means for transmitting a message representing the chronic obstructive pulmonary disease condition change indicator.

The system of any of the preceding paragraphs further comprising means for warning a user of the apparatus based on the chronic obstructive pulmonary disease condition change indicator.

The system of any of the preceding paragraphs further comprising a flow generator configured to generate a flow of breathable gas at a pressure above atmospheric pressure to a patient interface to satisfy a target ventilation.

The system of any of the preceding paragraphs wherein the target ventilation is an estimate of alveolar ventilation.

A device for monitoring a patient to evaluate a respiratory insufficiency condition of a patient comprising: a sensor to generate a signal associated with a pressure therapy treatment of the respiratory system of patient; and a processor configured to control an evaluation of a severity change indicator based on a measure from the signal of the sensor, the severity change indicator representing information about a change in severity of a respiratory insufficiency condition of the patient.

The device of any of the preceding paragraphs wherein the measure represents the degree of respiratory assistance therapy determined from the signal of the sensor.

The device of any of the preceding paragraphs wherein the control of the evaluation of the severity change indicator includes assessing detected data associated with inspiratory flow limitation to rule out upper airway obstruction.

The device of any of the preceding paragraphs wherein the control of the evaluation of the severity change indicator includes assessing a measure representing a respiratory rate.

The device of any of the preceding paragraphs wherein the control of the evaluation of the severity change indicator includes assessing a measure representing a respiratory duty cycle determined from the signal of the sensor.

The device of any of the preceding paragraphs wherein the control of the evaluation of the severity change indicator includes assessing a measure representing an intrinsic positive end expiratory pressure.

The device of any of the preceding paragraphs wherein the control of the evaluation of the severity change indicator includes assessing a measure representing an expiratory flow limitation.

The device of any of the preceding paragraphs wherein the measure represents a magnitude of a measured flow in a later portion of expiration that is determined from the signal of the sensor and wherein the control of the evaluation further assesses an insignificant change in respiratory rate or ventilation.

The device of any of the preceding paragraphs wherein the evaluation of the processor comprises determining a change of one or more earlier measures of the signal compared to one or more subsequent measures of the signal.

An apparatus adapted to determine the likelihood of an acute exacerbation occurring in a patient with respiratory insufficiency, comprising: at least one sensor adapted to measure at least one respiratory parameter of the patient; and a controller, coupled to the at least one sensor, wherein the controller is configured to evaluate the respiratory parameter measured at an at least one earlier first time with the respiratory parameter measured at a second time to determine when changes in the respiratory parameter are occurring, when a change in the respiratory parameter is determined the level of change and the length of time between the at least one first time and second time are evaluated to determine the likelihood of an acute exacerbation occurring.

The apparatus of any of the preceding paragraphs, wherein a larger level of change in the respiratory parameter and a longer length of time indicates a more likely occurrence of an acute exacerbation.

The apparatus of any of the preceding paragraphs wherein the change in the respiratory parameter is an increase over time.

The apparatus of any of the preceding paragraphs, wherein the respiratory parameter measured at a second time is evaluated with the respiratory parameter measured at multiple earlier first times to determine a change trend in the respiratory parameter over time.

The apparatus of any of the preceding paragraphs, wherein the controller is configured to provide a warning signal based on the determined likelihood of an acute exacerbation occurring.

The apparatus of any of the preceding paragraphs further comprising a flow generator adapted to provide positive pressure support to the patient.

The invention claimed is:

1. A device for monitoring a patient to evaluate a respiratory insufficiency condition of the patient comprising:
   a transducer to generate a signal representative of a pressure delivered by a flow generator; and
   a processor, coupled with the transducer, the processor configured to control an evaluation of a severity change indicator based on detecting, using a measure of determined pressure from the signal, a change in the measure of determined pressure from a plurality of treatment sessions, the evaluation comprising a detection of a continuous rise in the measure of determined pressure successively through the plurality of treatment sessions, the indicator representing information about a change in severity of a respiratory insufficiency condition of the patient,
   wherein the respiratory insufficiency condition is attributable to an insufficiency condition of the patient's lungs.

2. The device of claim 1 further comprising the flow generator configured to generate a flow of breathable gas at a pressure above atmospheric pressure to a patient interface, wherein the processor is configured to control the flow generator.

3. The device of claim 2 wherein the flow generator is configured to generate the flow of breathable gas at a pressure above atmospheric pressure to maintain a target ventilation, and wherein the measure of determined pressure comprises a measure of pressure generated by the flow generator in order to maintain the target ventilation.

4. The device of claim 3 wherein the target ventilation is a minute ventilation and the measure of determined pressure is an average pressure.

5. The device of claim 3 wherein the target ventilation is an estimate of alveolar ventilation.

6. The device of claim 3 wherein the evaluation of the severity change indicator comprises a threshold comparison of the continuous rise in the measure of determined pressure successively through the treatment sessions.

7. The device of claim 6 wherein the threshold comparison involves the measure of determined pressure from one of the plurality of treatment sessions and a prior measure of determined pressure used to maintain the target ventilation during a prior treatment session of the plurality of treatment sessions.

8. The device of claim 6 wherein the threshold comparison represents an indication of a repeated rise in the measure of determined pressure over a period of days.

9. The device of claim 6 wherein the threshold comparison involves a difference between the measure of determined pressure from one of the plurality of treatment sessions and a prior measure of determined pressure used to maintain the target ventilation during a prior treatment session of the plurality of treatment sessions.

10. The device of claim 6 wherein the threshold comparison includes a ratio of the measure of determined pressure from one of the plurality of treatment sessions and a prior measure of determined pressure used to maintain the target ventilation during a prior treatment session of the plurality of treatment sessions.

11. The device of claim 6 wherein the evaluation of the severity change indicator further comprises a further threshold comparison involving a determined respiratory rate and a prior respiratory rate.

12. The device of claim 11 wherein the further threshold comparison represents an indication of a repeated rise in the determined respiratory rate over a period of days.

13. The device of claim 6 wherein the processor is configured to activate a warning based on the severity change indicator.

14. The device of claim 13 wherein the warning comprises an activated light.

15. The device of claim 13 wherein the warning comprises a message.

16. The device of claim 1 wherein the processor is configured to control transmitting of an electronic message including data representing a result of the evaluation of the severity change indicator.

17. The device of claim 3 further comprising a transmitter coupled with the processor, wherein the processor is further configured to control transmitting of a message including data representing the severity change indicator.

18. A system for monitoring a patient to evaluate a respiratory insufficiency condition of the patient comprising:
a pressure means to generate a signal representative of the pressure delivered by a flow generator; and
processing means for controlling an evaluation of a severity change indicator based on detecting, using a measure of determined pressure from the signal, a change in the measure of determined pressure from a plurality of treatment sessions, the evaluation comprising a detection of a continuous rise in the measure of determined pressure successively through the plurality of treatment sessions, the indicator representing information about a change in severity of a respiratory insufficiency condition of the patient,
wherein the respiratory insufficiency condition is attributable to an insufficiency condition of the patient's lungs.

19. The system of claim 18 further comprising means for transmitting a message representing the indicator.

20. The system of claim 18 further comprising means for warning a user of the system based on the indicator.

21. The system of claim 18 further comprising the flow generator configured to generate a flow of breathable gas at a pressure above atmospheric pressure to a patient interface to satisfy a target ventilation.

22. The system of claim 21 wherein the target ventilation is an estimate of alveolar ventilation.

23. A device for monitoring a patient to evaluate a respiratory insufficiency condition of a patient comprising:
a sensor to generate a signal associated with a pressure therapy treatment of the respiratory system of a patient; and
a processor configured to control an evaluation of a severity change indicator based on detecting, using a measure of determined pressure from the signal, a change in the measure of determined pressure from the signal of the sensor from a plurality of treatment sessions, the evaluation comprising a detection of a continuous rise in the measure of determined pressure successively through the plurality of treatment sessions, the severity change indicator representing information about a change in severity of a respiratory insufficiency condition of the patient,
wherein the respiratory insufficiency condition is attributable to an insufficiency condition of the patient's lungs.

24. The device of claim 23 wherein the measure of determined pressure represents a degree of respiratory assistance therapy determined from the signal of the sensor.

25. The device of claim 24 wherein the control of the evaluation of the severity change indicator includes assessing detected data associated with inspiratory flow limitation to rule out upper airway obstruction.

26. The device of claim 23 wherein the control of the evaluation of the severity change indicator includes assessing a measure representing a respiratory rate.

27. The device of claim 23 wherein the control of the evaluation of the severity change indicator includes assessing a measure representing a respiratory duty cycle determined from the signal of the sensor.

28. The device of claim 23 wherein the control of the evaluation of the severity change indicator includes assessing a measure representing an intrinsic positive end expiratory pressure.

29. The device of claim 23 wherein the control of the evaluation of the severity change indicator includes assessing a measure representing an expiratory flow limitation.

30. The device of claim 23 wherein the measure of determined pressure represents a magnitude of a measured flow in a later portion of expiration that is determined from the signal of the sensor and wherein the control of the evaluation further assesses a change in respiratory rate or ventilation.

31. The device of claim 23 wherein the evaluation of the processor comprises determining a change of one or more earlier measures of the signal compared to one or more subsequent measures of the signal.

32. The device of claim 1,
wherein, in the evaluation, a level of the change between first and second measures of determined pressure from successive treatment sessions of the plurality of treatment sessions is compared with at least one threshold related to a continuous rise successively in the measure of determined pressure.

* * * * *